United States Patent
Hetherington

(10) Patent No.: US 8,540,681 B2
(45) Date of Patent: Sep. 24, 2013

(54) INJECTION CONTROL DEVICE WITH GEARING MECHANISM

(75) Inventor: Hugh E. Hetherington, Bozeman, MT (US)

(73) Assignee: BSECS Holdings, LLC, Bozeman, MT (US)

( * ) Notice: Subject to any disclaimer, the term of this patent is extended or adjusted under 35 U.S.C. 154(b) by 1206 days.

(21) Appl. No.: 12/379,924

(22) Filed: Mar. 4, 2009

(65) Prior Publication Data

US 2009/0254048 A1  Oct. 8, 2009

Related U.S. Application Data

(63) Continuation-in-part of application No. 12/078,603, filed on Apr. 2, 2008, now Pat. No. 8,133,208.

(51) Int. Cl.
*A61M 5/00* (2006.01)

(52) U.S. Cl.
USPC ............................ 604/208; 604/207; 604/218

(58) Field of Classification Search
USPC .................. 604/207, 208, 218, 36, 38, 93.01, 604/181, 186, 187, 228, 209, 210, 211, 131, 604/154, 155
See application file for complete search history.

(56) References Cited

U.S. PATENT DOCUMENTS

2006/0258990 A1* 11/2006 Weber ........................... 604/208
2007/0060894 A1*  3/2007 Dai et al. ...................... 604/207

* cited by examiner

*Primary Examiner* — Kevin C Sirmons
*Assistant Examiner* — Laura Schell
(74) *Attorney, Agent, or Firm* — TechLaw LLP; Jonathan A. Kidney

(57) ABSTRACT

An injection control device having a metered/controlled injection rate, that is proportional to the rate of withdrawal/injection—suitable for cosmetic as well as other applications—is described. For an injection mode, after the cannula is advanced into an object, the cannula is withdrawn to create a tract or tunnel within the targeted area. As the cannula is withdrawn, filler material in the injection control device is uniformly deposited into the tract or tunnel via the automatic metering system. The automatic metering system incorporates a syringe activating mechanism coupled to a gearing system which is capable of proportioning the deposition (or sucking) rate to the retraction/injection rate of the cannula. Accordingly, more consistent and uniform distribution (or harvesting) of material can be achieved with less cannula passes as well as requiring less dependence on the skills of the practitioner of this device.

7 Claims, 8 Drawing Sheets

INJECTION CONTROL DEVICE WITH GEARING MECHANISM

CROSS REFERENCE TO RELATED APPLICATIONS

This application is a Continuation-In-Part of U.S. patent application Ser. No. 12/078,603, filed Apr. 2, 2008, now U.S. Pat. No. 8,133,208, and claims benefit to the priority thereof. The contents therein being incorporated herein by reference in its entirety.

FIELD OF THE INVENTION

This disclosure relates to a gearing mechanism for a device for controlling an injection rate. More particularly, this disclosure relates to a worm-gear mechanism for automatically controlling the rate of injection of material as the cannula is metered in an injection control device.

BACKGROUND OF THE INVENTION

The aging process results in atrophy of the subcutaneous fat of the face. The skin looses its elasticity which along with the volume loss results in sagging and wrinkling of the facial skin. These changes can be found to occur in other parts of the body.

The traditional method for correcting the stigmata of dermatological aging is to excise, redrape and tighten the displaced skin. However, this approach does not adequately address the loss of volume and in some instances may exacerbate the appearance of aging. To address this concern, practitioners often use filler materials or implants placed under the skin's surface to reshape and re-volumize the contour. Numerous filler materials have been developed, however, in many aspects, grafted, autogenous fat is the ideal filler material. Fat cells are fragile and expiration of the cells may occur if they are not evenly distributed within the tissue and in small parcels. The current method of injecting filler materials is to manually inject using a syringe and needle (or cannula). This method is subject to human error and can result in uneven results, and in the case of fat, unpredictable survival.

Accordingly, there has been a long standing need in the discipline to devise systems and methods for addressing the problems discussed above.

SUMMARY

The foregoing needs are met, to a great extent, by the present disclosure, wherein methods and systems are provided that in some embodiments permit a controlled metering of injection material into an object.

In accordance with one aspect of the present disclosure, methods and systems are described which provide an injection control device (ICD), comprising: a body; a positioning guide; a syringe supporting section coupled to the body; a plunging member; and a plunging member activating system coupled to the positioning guide and the plunging member, wherein the activating system contains a main gear, and a worm gear in contact with the main gear and the positioning guide, wherein as the body of the ICD is moved away from a position of the positioning guide, the worm gear rotates causing the main gear to rotate, causing the plunging member to move forward within and relative to the body of the ICD.

In accordance with another aspect of the present disclosure, an injection control device is provided, comprising: means for gripping; means for positioning; means for supporting a syringe in the gripping means; means for plunging; and means for gearing to cause motioning of the means for plunging, being coupled to the means for positioning and the means for plunging, wherein as the means for gripping is moved away from a position of the means for positioning subject, the means for gearing is configured to cause the means for plunging to move forward within and relative to the body of the ICD.

DETAILED DESCRIPTION OF THE DRAWINGS

Figure 1:
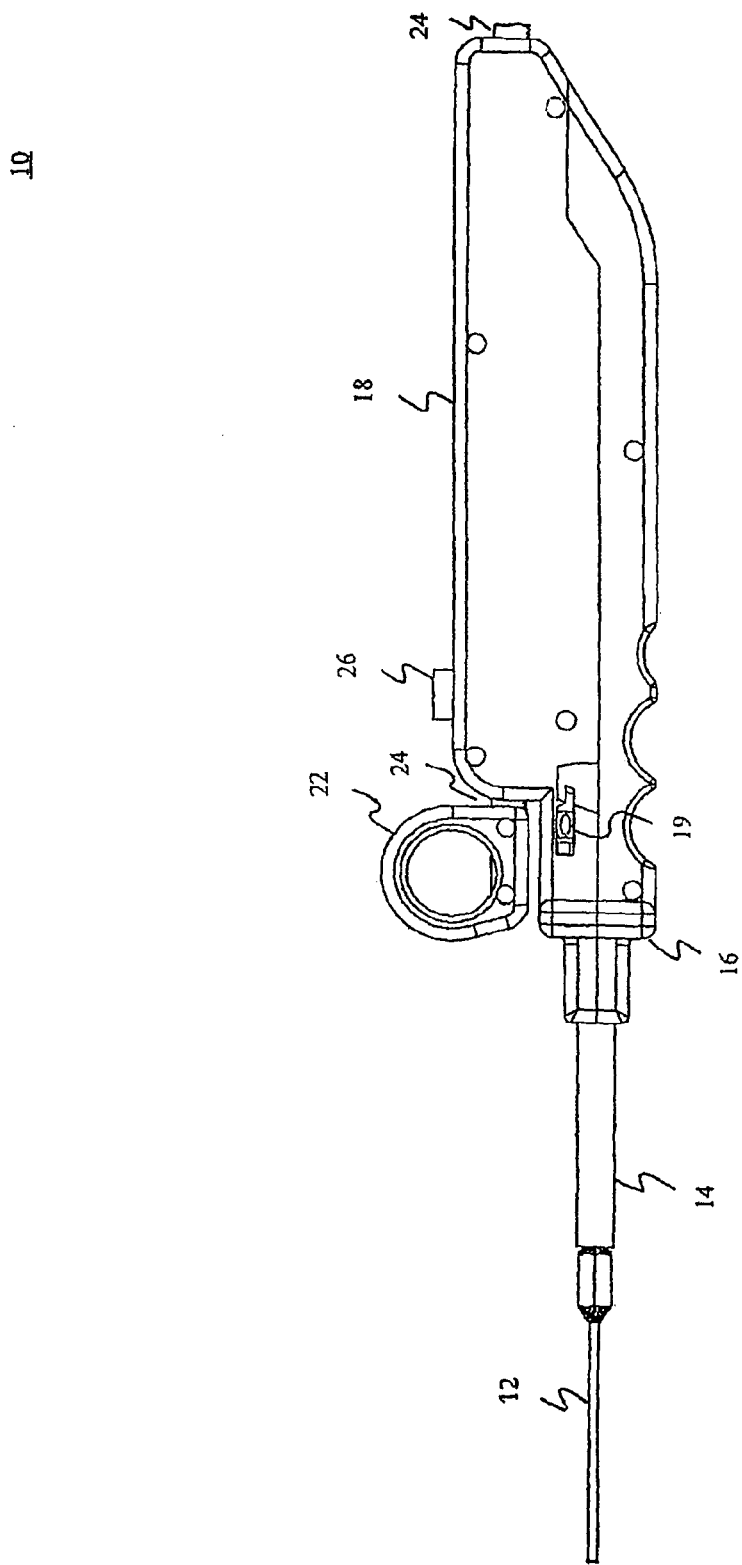
FIG. 1 is an illustration of a side view of an exemplary injection control device according to an embodiment of the invention.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that such subject matter may be practiced without these specific details.

As discussed above, many different filler materials have been used for tissue augmentation. Permanent fillers such as silicone are known to be unpredictable, the inflammatory reaction can be difficult to manage and they are difficult to remove if overcorrection occurs. Absorbable fillers are much safer but need to be re-injected on a recurring basis to maintain the result. In many ways, fat is the ideal subcutaneous filler because it is a living autologous tissue and can be removed if overcorrection occurs. However, fat cells are fragile and the augmentation may be temporary if a significant proportion of the fat cells die.

To maximize the survival of injected fat cells, the fat cells must be evenly distributed through the recipient tissue in small parcels. The parcels must be small enough that they can obtain adequate nutrition through plasmatic imbibition until such time as neovascularization of the fat parcels occurs. To accomplish this, the cannula is passed through the tissue multiple times, depositing a small amount of fat with each pass.

The conventional method of injecting fat and other filler materials is to manually advance the plunger into the syringe as the cannula is withdrawn from the tissue. The key to maximizing survival of the grafted fat is to make many passes. An insufficient number of passes will result in resorption of a portion of the fat cells. An excessive number of passes results in prolonged swelling of the tissue often taking several months to resolve. The prolonged swelling and variable results discourages the use of facial fat grafting. It is also difficult to manually gauge the amount of fat injected with each pass of the cannula.

In an attempt to address this difficulty, some practitioners have used a ratchet gun to inject the fat. However, the trigger mechanism associated with a ratchet gun injects a small amount of fat each time the trigger is squeezed. It essentially functions like a caulking gun. This device allows the operator somewhat better control over the release of the fat into the tissue however, the amount of fat injected is not proportional with the distance that the cannula is passed through the tissue. Therefore, overly large amounts or overly small amounts of filler material or fat can be injected along the injection track. Thus, these attempts have not adequately addressed the problems inherent to traditional manual injection methods.

The exemplary devices and methods described herein provide effective solutions to difficulties of the prior art, wherein in various embodiments a controlled amount of filler material is automatically deposited with each pass of the cannula. In principle, the cannula is advanced into the tissue to create a tract or tunnel within the targeted area. Then, as the cannula is withdrawn, the filler material is uniformly deposited though the tract or tunnel via the automatic metering system. The automatic metering system incorporates a syringe activating mechanism coupled to a gearing system which proportions the deposition to the retraction of the cannula.

By use of the exemplary devices and methods described herein, more consistent and uniform distribution of the material injected can be achieved with less cannula passes as well as having less dependence on the skills of the individual surgeon. Additionally, it should be appreciated that though the exemplary embodiments described herein are within the context of using fat as the filler material, other filler materials, whether organic or non-organic, living or non-living, may be used without departing from the spirit and scope of this invention.

It should be also appreciated that, in addition to the benefits listed above, by minimizing the number of cannula passes in the tissue, less trauma is effectuated upon the tissue, resulting in less swelling in the patient's body. Moreover, by metering the amount of fat (filler material) in the injection areas, less filler material is necessary to achieve the desired results. These and other advantages will be made more evident in the forthcoming sections.

FIG. 1 is an illustration of a side view 10 of an exemplary injection control device according to an embodiment of the invention. The exemplary injection control device is illustrated with a cannula or needle 12 coupled to a cannula mating section 14. It should be apparent that the cannula 12 may be removable or be of a disposable form. The cannula mating section 14 may be referred to as the syringe of the exemplary injection control device. The syringe 14 may be configured to be supported and/or held securely by a syringe-supporting section 16 of the body 18. The syringe 14 may also be disposable, if so desired, and may be configured in varying sizes, according to design or application preference. Accordingly, the syringe supporting section 16 may be configured to be adapted to various shapes or sizes of the syringe 14, according to design or application preference. While the cannula 12 is illustrated as having a straight shape, other curvatures or shapes may be used according to application preference.

The body 18 is illustrated as containing a latch 19 which operates to secure the upper and lower portions of the body 18, during assembly. The body 18 accommodates an exposed ring 22 which is connected to a positioning rack 24 (partially obscured) which is housed or protected by the body 18. The positioning rack 24 is shown in FIG. 1 as being situated to travel through the body 18 and is subject to engagement of the brake 26. In some embodiments, the positioning rack 24 may be placed exterior of the body 18, according to design preference, such as, for a non-limiting example, a sliding arrangement as seen in older slide rules. The brake 26 operates to prevent travel of the positioning rack 24 when engaged, or conversely, when dis-engaged, depending on design implementation.

While FIG. 1 illustrates the exposed ring 22 as being circular in shape, it should be understood that other shapes, closed or open, may be used without departing from the spirit and scope of this invention. In fact, in some embodiments, it may be desirable to have a "flat" surface or "plate" rather than the exposed ring 22, depending on the practitioner's preference or application.

Figure 2:
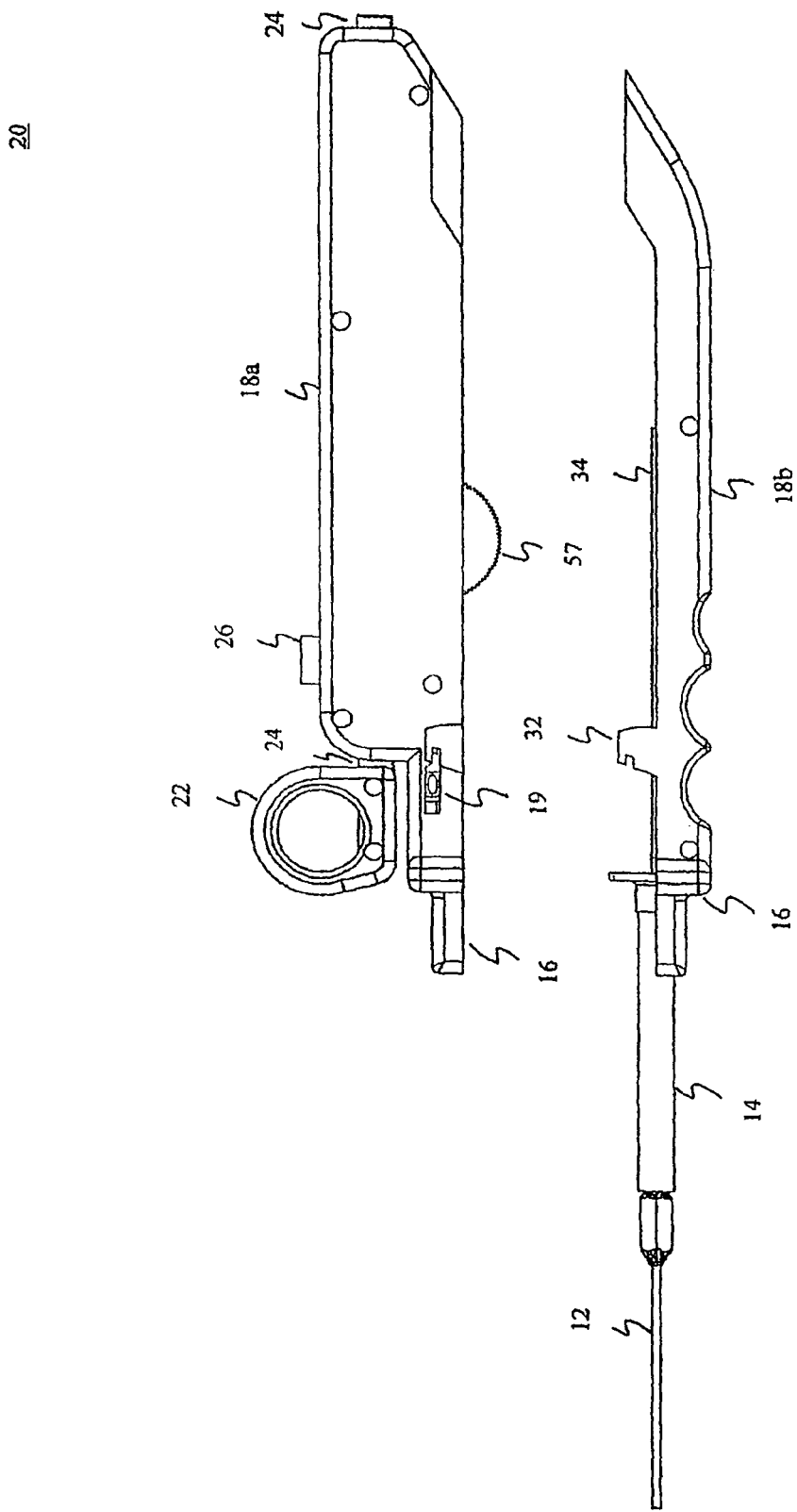
FIG. 2 is an illustration of a side view of a separated exemplary injection control device of FIG. 1

FIG. 2 is an illustration of a side view 20 of the exemplary injection control device of FIG. 1 with the upper body portion 18a and lower body portion 18b of the body 18 separated. Of note is the exposed latch engagement member 32 used for attachment to the latch 19 when the upper body portion 18a and lower body portion 18b are attached to each other. Also, FIG. 2 illustrates the lower portion of the exposed syringe rack gear 57 and the upper portion of the corresponding syringe rack 34. It should be appreciated that other forms of the latch engagement member 32 may be used than that shown in FIG. 2. That is, instead of latching with a slidable latch 19, a twisting or screwing, or otherwise engaging motion may be used with an appropriately designed latch engaging member 32, to achieve the desired securing operation, without departing from the spirit and scope of this invention. Therefore, other devices or mechanisms known in the art for securing the upper portion 18a and the lower portion 18b of the body 18 may be contemplated, according to design or efficiency preference.

Further, it should be appreciated that the exemplary embodiment shown in FIG. 2 may also be configured so that the body 18 is separated into a different configuration, such as to be arranged in "left" and/or "right", or other arrangements, as opposed to "upper" and/or "lower", etc. Therefore, it should be apparent that other shapes, whether paired or multiplied, or separation methodologies ranging from sliding, twisting, screwing, snapping, etc., for example, may be used to enable the practitioner to access the interior of the exemplary injection control device. It should also be appreciated that in some embodiments, a gripping portion may be provided on the surface of the body 18 to enable a practitioner a secure hold of the exemplary injection control device.

Additionally, while the exemplary injection control device is shown in FIG. 2 with a body 18 that may be separated, it is contemplated that a uni-body implementation may be used. That is, the body 18 may be formed as a single piece, not separable wherein the syringe 14 is "attached" to the body 18. Thus, a single body configuration may be made without departing from the spirit and scope of this subject matter.

Figure 3:
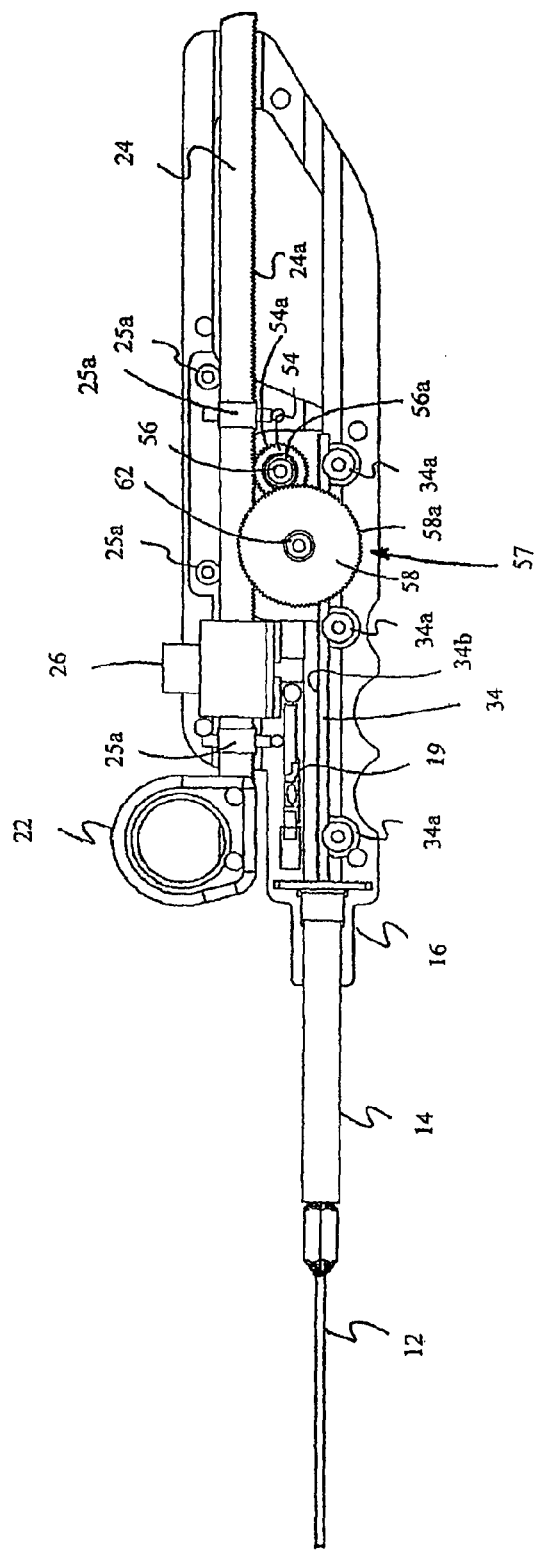
FIG. 3 is an illustration of a cut-away view of the exemplary injection control device of FIG. 1.

FIG. 3 is an illustration of an axial cut-away view 30 of the exemplary injection control device of FIG. 1. The cut-away view 30 reveals an exemplary gearing arrangement suitable for accomplishing at least one of the goals of the exemplary injection control device. For example, using the gearing arrangement shown in FIG. 3, it should be apparent to one of ordinary skill in the art that during the operation of the exemplary injection control device, as the ring 22 is fixed in place and the body of the injection control device is moved to the "right," the syringe rack 34 will move to the "left"—acting as a plunger into the syringe 14 being held in the syringe supporting section 16. Therefore, any filler material in the syringe 14 will be expelled into the cannula 12. Based on appropriate gearing ratios of the exemplary gearing arrangement, a very precise and controlled injection of the filler material can be accomplished, with minimal technical expertise.

In an exemplary embodiment of the injection control device, the gearing arrangement of FIG. 3 is illustrated with the primary components of the positioning rack 24, engaging a positioning rack gear assembly 55. The positioning rack gear assembly 55 having an outer gear 54 and inner gear 56 and clutch (not seen) is coupled to a syringe rack gear 57 having an outer gear 58 and an inner gear 62 (not seen), which is engaged to the syringe rack 34. The positioning rack 24 is constrained and guided by positioning rack rollers/guides 25a, which are placed at strategic points along the travel area of the positioning rack 24, to guide and maintain smooth travel of the positioning rack 24 through the body 18. Similarly, syringe rack rollers/guides 34a are illustrated as guiding and/or constraining the syringe rack 34 within the body 18.

It should be appreciated that while FIG. 3 illustrates various rollers/guides 25a and 34a, disposed within and about the body 18, other forms or arrangements of rollers/guides that are known in the art or future-derived, may be used to achieve the desired effects, without departing from the spirit an scope of this invention. In fact, in some embodiments, the roller/guides 25a and 34a may be supplanted with full body guides along the body 18, such as a channel or sleeve. Since knowledge of such presently known rollers/guides and alternative arrangements are within the purview of one of ordinary skill in the art, they are not discussed herein.

In one mode of operation, the ring 22 (also known as the positioning guide) is held stationary with respect to the skin. The body 18 of the injection control device is moved as the cannula 12 is withdrawn. In another mode of operation, it may be desirable to advance the entire injection control device as a unit as the cannula 12 is advanced into the tissue. Then the ring 22 is held stationary with respect to the skin as the body 18 of the injection control device with the syringe 14 and cannula 12 is withdrawn expelling the filler material. The ring 22 is then pushed back into the body 18 of the injection control device. The entire injection control device is then again advanced as a unit.

In another mode of operation, the reverse effect can be accomplished, wherein by advancing the cannula 12 into the skin, material can be "sucked" into the injection control device. Therefore, as will be apparent from the description provided herein, multiple modes of operations may be contemplated, accordingly, the injection control device may also operate as a suction control device.

In view of various movements of the body 18 with respect to the ring/positioning guide 22, the positioning rack's teeth 24a will engage with the teeth 54a of the outer gear 54 of the positioning rack gear assembly 55 and cause rotation. The positioning rack gear assembly 55 may be configured with teeth ratios to act as a reduction gear in order to translate the linear displacement of the positioning rack 24 to a reduced linear displacement of the syringe rack 34. As the teeth 56a of the inner gear 56 of the positioning rack gear assembly 55 engage with the teeth 58a of the outer gear 58 of the syringe rack gear 57, the teeth 62a (not shown) of the inner gear 62 (not shown) will engage the teeth 34b of the syringe rack 34, causing a linear displacement of the syringe rack 34.

In an exemplary embodiment of the injection control device, a ratio of approximately 5.2093:1 was used to effect the desired movement of the positioning rack 24 with respect to the syringe rack 34. That is, for every 5.2093 inches the injection control device is displaced or "withdrawn" from the tissue with the ring 22 held in place, the syringe rack 34 advances approximately 1 inch. Given a commercially available 1 cc syringe, the exemplary injection control device will inject approximately 0.00436 cubic inches of filler material for every one inch the cannula 12 is withdrawn from the tissue.

The gearing ratio described above may be adjusted according to methods and systems known in the art of gearing. Therefore, the gearing ratio may be adjusted by simply replacing the appropriate gears and racks to achieve a desired injection rate. In such embodiments, a "dialing" in of a different gear ratio may be contemplated, according to gearing systems known in the art. Alternatively, to achieve a different or variable injection rate, varying syringes with different bore diameters may be used, to increase or decrease the rate of material injected. If the outside diameter of the syringe is held constant while the internal diameter is varied, this will allow the effective gear ratio or "injection rate" to be easily varied according to the application. This can prove to be a very economical way of "changing gears" without changing the actual gearing of the injection control device or switching to a similar injection control device with a different gear ratio.

As is made apparent from the above description, one mode operation of the exemplary injection control device may entail the practitioner positioning the injection control device with the ring 22 (operating as a positioning guide) against the skin or a pre-determined distance from the skin of a patient. With the ring 22 (positioning guide) held in a stationary position, the body 18 of the injection control device can be advanced into the tissue surrounding the skin and then withdrawn, with the ring 22 (positioning guide) held in place. Consequently, the advancing motion of the cannula 12 will create a tract in the tissue, while the withdrawing motion of the cannula 12 (the body 18 of the injection control device) will deposit the filler material in the void created in the tract as the cannula 12 is withdrawn.

In order for the ring 22 to be fixed at a desired position in proximity to the skin or surface of the tissue, the ring 22 should be allowed to be manipulated in a "forward" or skin-side direction without causing the syringe rack 34 to move. This freedom is achieved by a clutching mechanism that is discussed in further detail below.

It should be appreciated that, in some embodiments, it may be desirable to have the ring 22 (positioning guide) flush to the skin, thus providing the stable reference of the skin surface or body surface for the practitioner to exert a "push" against while he is "pulling" the injection control device. Of course, it should be apparent that depending on the preferences and skills of the practitioner, the ring 22 may not placed against the skin or surface but at a preferred distance. For example, a practitioner may place his thumb into the ring 22 and use the span of his hand with his fingers or palm against the skin, resulting in the ring 22 being positioned a pre-determined distance from the surface of the tissue. Thus, it should be apparent that variations of the placement of the ring 22 as well as its shape may be practiced without departing from the spirit and scope of this invention.

Figure 4:
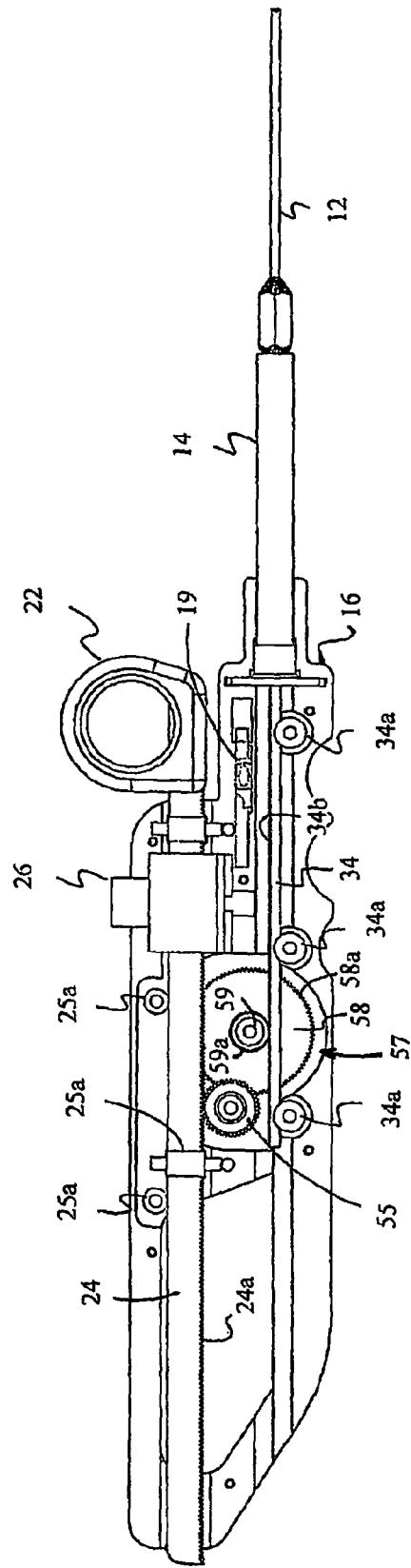
FIG. 4 is a close-up reverse illustration of the interior of the exemplary injection control device.

FIG. 4 is a close-up illustration 40 of the reversed side of the interior of the exemplary injection control device. FIG. 4 illustrates the teeth 59a of the syringe rack gear 57 engaging the teeth 34b of the syringe rack 34.

Figure 5:
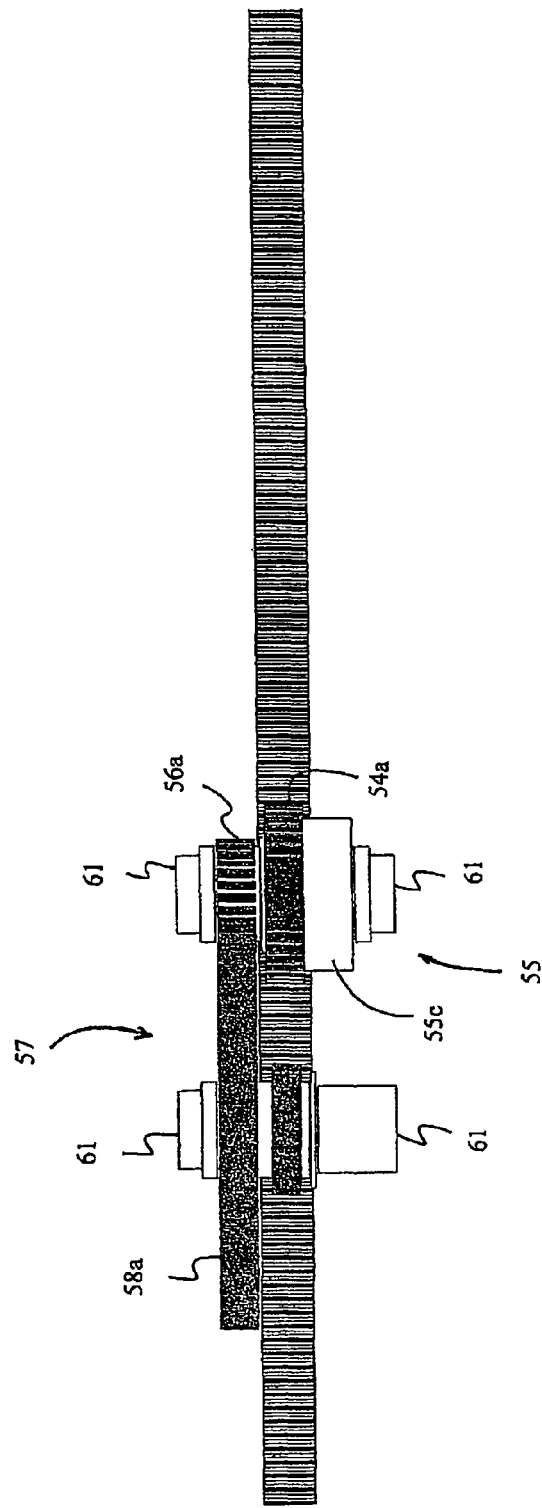
FIG. 5 is a bottom-side illustration of the exemplary injection control device with the syringe rack removed from view.

FIG. 5 is a bottom-side illustration 50 of the gear contacts of the exemplary injection control device with the syringe rack 34 removed from view. The positioning rack gear assembly 55 is shown with a clutch 55c which acts as an intermediary between the outer gear 54 and the inner gear 56 of the positioning rack gear assembly 55. The clutch 55c functions to provide a mechanism to enable "free" movement of the positioning rack 24 without causing the inner gear 56 of the positioning rack gear assembly 55 to move. Thus, the positioning rack gear may be moved in a preferred direction without causing the syringe rack gear 57 to turn. In principle, the clutch 55c allows advancement of the syringe plunger into the syringe cylinder but not its withdrawal. Therefore, the clutch 55c allows the exemplary injection control device to be advanced relative to the ring 22 without causing the plunger to move relative to the syringe cylinder.

As shown in FIG. 1, the brake 26 may be used to stop or engage the motion of the positioning rack 24. Therefore, by engaging the brake 26, the ring 22 may be secured while the cannula 12 is positioned in the tissue. It should be noted that the brake 26, in some embodiments may not be necessary, as operation of the injection control device can conceivably be executed without use of the brake 26.

In particular, the use of a clutch 55c or one-direction-engagement mechanism enables the practitioner to adjust the position or extension of the positioning rack 24 from the body 18, with the ring 22 at a desired distance from the patients' tissue, without causing the syringe rack 34 to move in a reverse orientation. The clutch 55c can be engaged in such a manner to cause the gear train to rotate and advance the syringe rack 34 (or plunger) into the syringe, as the body 18 of the injection control device is moved away from the ring 22. The clutch 55c allows the body 18 of the injection control device to move towards the ring 22 without the syringe rack 34 moving with respect to the syringe. Also, the clutch 55c can be configured to prevent the gear train from moving the syringe rack 34 with respect to the syringe as the body 18 is advanced with respect to the ring 22.

In some embodiments, the clutch 55c may be supplanted with an arrangement wherein the teeth 54a of the outer gear 54 are displaced from the teeth 24a of the positioning rack 24, by some switch or motion (not shown) that is coupled to the positioning rack gear assembly 55. Thus, by removing contact of the teeth 54a of the outer gear 54 from the teeth 24a of the positioning rack 24, the positioning rack 24 may be moved without causing the syringe rack 34 to move.

It should be appreciated that one of ordinary skill in the art of gearing may devise an alternative scheme for providing "free" movement of the positioning rack 24 in a preferred direction, or even in both directions. The above clutching mechanism 55c is provided as one simple scheme for achieving the desired results wherein more complicated or different schemes may be contemplated. Therefore, other schemes or systems for providing controlled motion or contactless motion may be used, whether using gears, clutches, slips, discs, springs, etc., without departing from the spirit and scope of this invention.

FIG. 5 also illustrates the use of gear axle caps 61 for the positioning rack gear assembly 55 and the syringe rack gear 57. It should be appreciated that in some embodiments, the gear axle caps 61 may not be necessary, as axle securing methods not consisting of caps 61 may be used, such as those that are common in the industry. Additionally, the illustrated spacing between the gears and rack(s) shown may be adjusted according to design preference.

Figure 6:
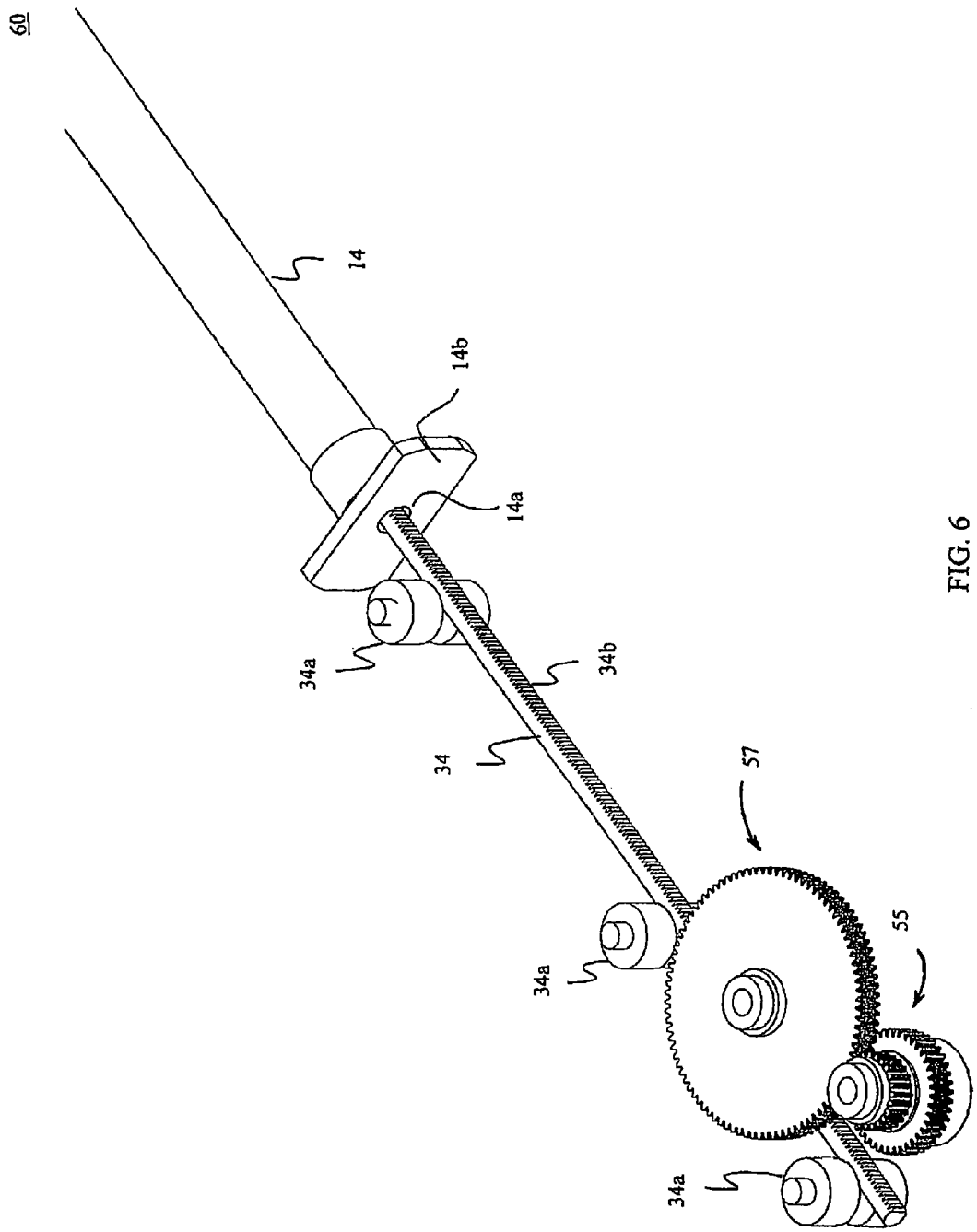
FIG. 6 is a perspective view illustration of the syringe rack arrangement of the exemplary injection control device.

FIG. 6 is a perspective view illustration 60 of the syringe rack arrangement. Specifically, the syringe rack 34 is illustrated with a smooth ridge 34b that fits within a channel within the roller/guides 34a. By use of the smooth ridge 34b within the channel, lateral movement of the syringe rack 34 can be minimized. Of course, in some embodiments, the roller/guides 34a may be replaced with bearings, if desired. Or, the ridge 34b may be replaced with a channel "under" the syringe rack 34, wherein bearings or roller/guides may be disposed. In some embodiments, the syringe rack 34 may have a different shape, according to design preference. Therefore, round, square, rectangular or other shapes may be used. Also, a non-bearing configuration, using for example, the interior of the body 18 as a constraining and guiding entity may be used. Therefore, alternative arrangements for guiding the syringe rack 34 may be used without departing from the spirit and scope of this invention.

The syringe rack 34 is also shown in FIG. 6 as having its "front" plunger end inside an opening 14a of the syringe 14. In some embodiments the syringe rack 34 may be configured to drive another mechanism that acts as a plunger for the opening 14a of the syringe 14. Thus, some form of pivoting may be designed to cause the syringe rack 34 to move "outside" the opening 14a, while still achieved the desired effect of moving a plunger into or out of the syringe 14. In some embodiments, the syringe rack 34 may be an integral part of the syringe 14. That is, the syringe rack 34 may constitute the actual plunger mechanism in the syringe, or a controlling member. Thus, a syringe 14 may be configured with a syringe rack 34 pre-configured for use with the injection control device. Alternatively, the syringe rack 34 may be configured with a geometry that is suitable for use with disposable syringes. Therefore, the injection control device may use disposable syringes or may use syringes having a plunger with a syringe rack 34 attached.

Figure 7:
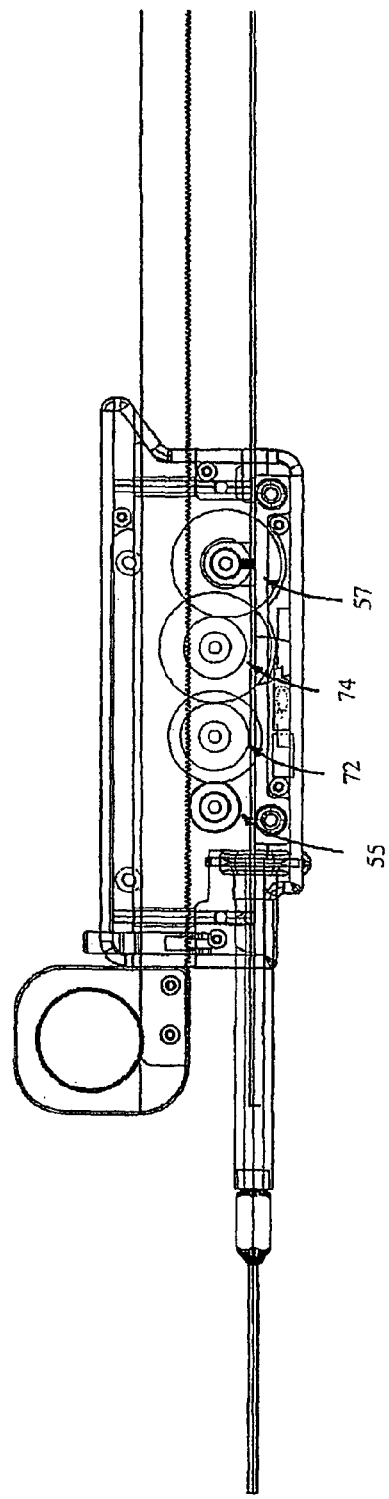
FIG. 7 is an illustration of an exemplary injection control device with multiple gears.

It should be noted that in FIG. 6, the anterior end of the syringe 14 is shown having flanges 14c. The typical syringe 14 is understood to have such flanges 14c, and therefore, the exemplary injection control device exploits the presence of the flanges 14c by accommodating them in bulged areas of the syringe supporting section 16. In some embodiments, the syringes 14 may not have such flanges 14c, therefore an appropriate securing mechanism may be devised, such as a clamp or well, for example, for securing the syringe 14 to the exemplary injection control device. In such embodiments, the flanges 14c may be of a reduced size and therefore, the upper body 18a and lower body 18b portions surrounding the flanges 14c may be altered in a manner suitable for achieving the desired effect, without departing from the spirit and scope of the invention FIG. 7 is an illustration 70 of the outline of an exemplary injection control device with multiple gears. Specifically, the exemplary injection control device is illustrated with four gears, chaining action from the first positioning rack gear assembly 55 to a series of "reduction" gears 72 and 74, to the syringe rack gear 34. By use of multiple gears 72 and 74, varying amounts of ratios can be achieved. Of course, while FIG. 7 illustrates a total of four gears in the gear train, more or less gears may be used according to design preference.

Figure 8:
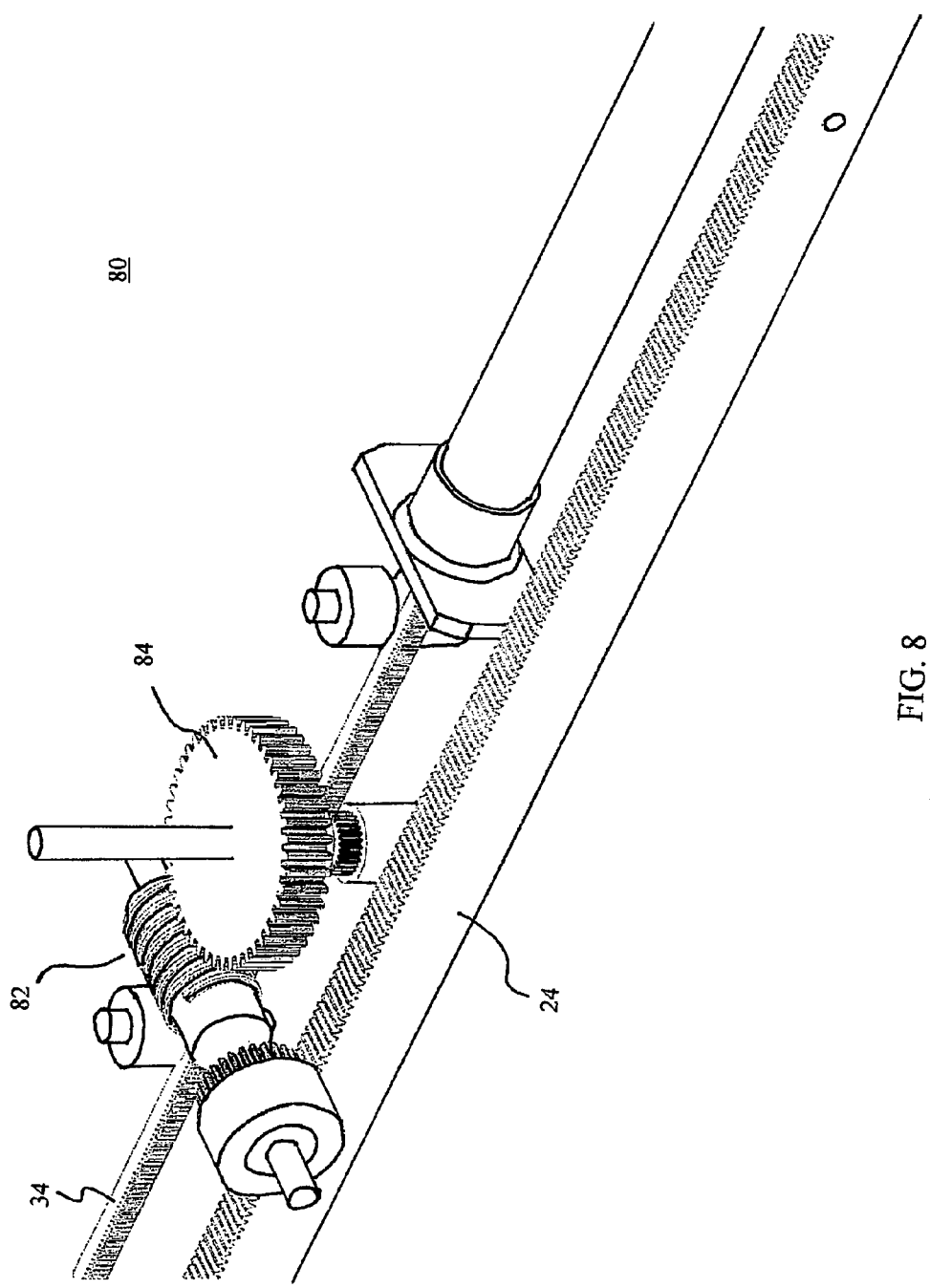
FIG. 8 is an illustration of an exemplary worm gear mechanism.

FIG. 8 is an illustration 80 of an exemplary gearing mechanism suitable for use in an exemplary injection control device. The exemplary gearing mechanism is configured as a worm gear 82 that, by movement of the positioning rack 24, engages the main gear 84. By rotation of the main gear 84 via the worm gear 82, the coupled syringe rack 34 can be moved, thus arriving at the movements described above. The exemplary worm gear 82 may include the clutching mechanism 55c described above, either incorporated inside the body of the worm gear 82 or as a part of the main gear 84. Accordingly, the worm gear 82 mechanism can be adapted to provide one-way motion of the syringe rack 34 for either injecting material or harvesting material. As discussed above, the exemplary injection control device may be configured to allow all possible combinations of movements between the body 18 of the exemplary injection control device and the syringe rack 34, as according to design preference.

It should be noted that the position of the worm gear 82 may be adjusted to where it is "forward" of the main gear 84, rather than aft of the main gear 84. Accordingly, modifications to the form and implementation of the worm gear 82 and attendant components of the injection control device may be made without departing from the spirit and scope of this disclosure.

By use of the exemplary injection control device several advantages can be obtained:

The injection of the filler material is substantially proportional to the length of the injection tract and uniform along the course of the injection tract;

An "automatic" controlled injection system can be used for fat grafting or injection of other filler materials;

Intracutaneous, subcutaneous and intramuscular injections of filler materials can be precisely controlled;

A fixed amount of fat or other filler material can be injected per unit distance traveled by the tip of the cannula;

The injection ratio (amount of material injected over a given distance of cannula withdrawal) can be varied by simply using varying bore diameter syringes;

The use of syringes (disposable); and

The use of syringes incorporating a rack in the plunger.

It should be appreciated that based on an understanding of the exemplary injection control device disclosed herein, several modifications may be contemplated without departing from the spirit and scope of this invention. As some cannulas may be of different diameters and openings, a volume approach may be achieved by adjusting the gearing, for example.

As another modification, the clutch 55c may be configured to operate in a "reverse" manner than described. That is, rather than having the exemplary injection control device inject filler material, the exemplary injection control device may be configured to "suck" filler material. Thus, in some applications, harvesting of fat or filler material may be accomplished by altering the clutching or gearing of the exemplary injection control device.

Along the lines of the above modification, it is possible to design a gearing system that injects filler material as the cannula is advanced, rather than withdrawn. Additionally, the exemplary injection control device may be configured with opposing gear trains that would enable the injection of filler material as the cannula is advanced as well as when the cannula is withdrawn. Similarly, the exemplary injection control device may operate in a manner to enable the withdrawal or sucking of filler material as the cannula is advanced as well as when the cannula is withdrawn.

While the exemplary injection control device is shown in the above Figures as requiring manual movement to effect the travel of the filler material, it should become apparent, based on this disclosure, that automatic movement may be effected by a motor. Thus, the linkage between the various parts may be substituted by a motor or electromechanical device. Similarly, a hydraulic system for controlled the injection rate or suction rate may be implemented without departing from the spirit and scope of this invention. By use of an electromechanical device or system, the exemplary injection control device may be easily adapted to larger volume operations, such as, breast and buttock augmentation. Additionally, an alternative "gearing" mechanism may be desired, non-limiting examples being springs, spring motor, screw type racks or worm gears, as well as piezoelectric travel engines, and so forth.

It will be understood that many additional changes in the details, materials, steps and arrangement of parts, which have been herein described and illustrated to explain the nature of the disclosure, may be made by those skilled in the art within the principle and scope of the disclosure as expressed in the appended claims.

What is claimed is:

1. An injection control device (ICD), comprising:
an external body having a distal and proximal end;
a syringe supporting section coupled to the body;
a transmission system coupled to the body, the transmission system containing a main gear, and a worm gear in contact with the main gear;
a transmission system activating member housed within the external body, operably coupled and in contact with the main gear of the transmission system and linearly extendable from the distal end of the body beyond a distal end of the syringe supporting section; and
a plunging member coupled to the transmission system,
wherein the transmission system, activating member, and plunging member are configured so that a motion of the body of the ICD from a substantially fixed position of the activating member and the activating member's contact with the worm gear, causes the main gear to rotate, forcing a one-way motion of the plunging member to inject or aspirate material contained in the device, as the body of the ICD is moving, a rate of injection or aspiration being proportional to an amount of movement of the body of the ICD.

2. The injection control device of claim 1, further comprising:
a syringe supported by the syringe supporting section; and
a cannula coupled to the syringe.

3. The injection control device of claim 1, wherein the transmission system contains a clutch, the clutch enabling movement of the activating member without causing movement of the plunging member.

4. The injection control device of claim 1, further comprising a brake to secure the activating member from movement.

5. The injection control device of claim 1, wherein the body is configured into at least two pieces which can be released from each other and secured to each other via a securing mechanism.

6. The injection control device of claim 1, wherein the transmission system is configured to move the plunging member in a same direction of movement as the body to provide the aspiration or injection.

7. The injection control device of claim 1, wherein the transmission system is configured to move the plunging member in an opposite direction of movement as the body to provide the aspiration or injection.

* * * * *